United States Patent [19]

Kempe

[11] Patent Number: 4,644,054
[45] Date of Patent: Feb. 17, 1987

[54] CALCITONIN ANALOGS WITH AMINO ACID SUBSTITUENTS AT POSITION 31

[76] Inventor: Tomas G. Kempe, 16604 Windermere Pl., Minnetonka, Minn. 55345

[21] Appl. No.: 782,494

[22] Filed: Oct. 1, 1985

[51] Int. Cl.⁴ .................. C07K 7/36; A61K 37/24
[52] U.S. Cl. .................................... 530/307; 514/808
[58] Field of Search ............ 260/112.5 T; 530/307; 514/808

[56] References Cited

U.S. PATENT DOCUMENTS 3,929,758 12/1975 Hughes et al. ............... 260/112.5 R

OTHER PUBLICATIONS

Rittel et al., *Experientia*, 15(2), 273–275 (1975).
Guttmann, *Calcitonin* 1980, Proceedings of an International Symposium held in Milan, Oct. 15–17, 1980.

*Primary Examiner*—Delbert R. Phillips
*Attorney, Agent, or Firm*—James R. Haller; Mary P. Bauman

[57] ABSTRACT

New polypeptides are disclosed which have biological activity of the same degree as known calcitonins and which have amino acid substituents in position 31 instead of the naturally occuring amino acids—Thr, Ala, Val.

11 Claims, No Drawings

CALCITONIN ANALOGS WITH AMINO ACID SUBSTITUENTS AT POSITION 31

FIELD OF THE INVENTION

This invention relates to calcitonin analogs having biological activity and to peptides which can be converted to biologically active calcitonin analogs.

BACKGROUND OF THE INVENTION

There is a wide variation in activity in the naturally occuring calcitonins with an approximate 40-fold range in biopotency. All calcitonins share common structural features. Each is 32 amino acids long with a C-terminal prolinamide and an N-terminal disulfide linked ring from position 1 through 7. Salmon 1 calcitonin, for example, has the following formula (Niall, H. D. (1969) Proc. Natl. Acad. Sci. USA 64, 771-778):

```
    ┌─────────────────────────────────────┐
H2N—Cys—Ser—Asn—Leu—Ser—Thr—Cys—Val—Leu—
     1   2   3   4   5   6   7   8   9

—Gly—Lys—Leu—Ser—Gln—Glu—Leu—His—Lys—
     10  11  12  13  14  15  16  17  18

—Leu—Gln—Thr—Tyr—Pro—Arg—Thr—Asn—
     19  20  21  22  23  24  25  26

—Thr—Gly—Ser—Gly—Thr—Pro—NH2
                 27  28  29  30  31  32
```

Other calcitonins occuring in nature resemble salmon 1 calcitonin in varying degrees (Queener, S. F. and Bell, N. H. (1975) Metabolism 24, 555-567; Lasmoles, F. et al. (1985) FEBS Lett. 180, 113-116). In eel, ovine, bovine, porcine and chicken calcitonins the amino acid threonine occupies position 31. The same position 31 is occupied by the amino acid alanine in human and murine calcitonins. Salmon 2 calcitonin and salmon 3 calcitonin both have valine at position 31.

Eel calcitonin differs from salmon 1 calcitonin by having the amino acids Asp at position 26, Val at position 27 and Ala at position 29. Chicken calcitonin differs from salmon 1 calcitonin by having the amino acid Ala at position 2, Ser at position 3, Asp at position 26, Val at position 27 and Ala at position 29. Salmon 2 calcitonin differs from salmon 1 calcitonin by having Asp at position 15, Phe at position 22, Ala at position 29 and Val at position 31. Salmon 3 calcitonin differs from salmon 1 calcitonin by having Met at position 8, Asp at position 15, Phe at position 22, Ala at position 29 and Val at position 31.

The calcitonins of mammalian origin differ more markedly from salmon 1 calcitonin, as shown by the following comparison. The disulfide linkage between positions 1 and 7 is omitted from the following sequence for clarity.

| Position: | 1 | 2 | 3 | 4 | 5 | 6 | 7 |
|---|---|---|---|---|---|---|---|
| Salmon 1 | Cys | Ser | Asn | Leu | Ser | Thr | Cys |
| Human | " | Gly | " | " | " | " | " |
| Murine | " | " | " | " | " | " | " |
| Bovine | " | Ser | " | " | " | " | " |
| Porcine | " | Ser | " | " | " | " | " |
| Ovine | " | Ser | " | " | " | " | " |

| Position: | 8 | 9 | 10 | 11 | 12 | 13 | 14 |
|---|---|---|---|---|---|---|---|
| Salmon 1 | Val | Leu | Gly | Lys | Leu | Ser | Gln |
| Human | Met | " | " | " | Thr | Tyr | Thr |
| Murine | " | " | " | " | " | " | " |
| Bovine | Val | " | Ser | " | Ala | " | Trp |
| Porcine | " | " | " | " | " | " | " |
| Ovine | " | " | " | " | " | " | " |

| Position: | 15 | 16 | 17 | 18 | 19 | 20 | 21 |
|---|---|---|---|---|---|---|---|
| Salmon 1 | Glu | Leu | His | Lys | Leu | Gln | Thr |
| Human | Asp | Phe | Asn | " | Phe | His | " |
| Murine | " | Leu | " | " | " | " | " |
| Bovine | " | " | " | Asn | Tyr | " | Arg |
| Porcine | Asn | " | " | " | Phe | " | " |
| Ovine | Asp | " | " | " | Tyr | " | " |

| Position: | 22 | 23 | 24 | 25 | 26 | 27 | 28 |
|---|---|---|---|---|---|---|---|
| Salmon 1 | Tyr | Pro | Arg | Thr | Asn | Thr | Gly |
| Human | Phe | " | Gln | " | Ala | Ile | " |
| Murine | " | " | " | " | Ser | " | " |
| Bovine | " | Ser | Gly | Met | Gly | Phe | " |
| Porcine | " | " | " | " | " | " | " |
| Ovine | Tyr | " | " | " | " | " | " |

| Position: | 29 | 30 | 31 | 32 |
|---|---|---|---|---|
| Salmon 1 | Ser | Gly | Thr | Pro—NH2 |
| Human | Val | " | Ala | " |
| Murine | " | " | " | " |
| Bovine | Pro | Glu | Thr | " |
| Porcine | " | " | " | " |
| Ovine | " | " | " | " |

The structural features responsible for the increased potency of ultimobronchial calcitonins (e.g., salmon calcitonin) relative to calcitonins of mammalian origin have not yet been fully determined. However, a human calcitonin analog with Serine[29] and Threonine[31] substituents has been reported to be five times more active than the natural human calcitonin. (Maier, R. et al. (1974) FEBS Lett. 48, 68-71). In salmon 1 calcitonin serine appears at position 29 and threonine appears at position 31 and salmon 1 calcitonin is thirty to forty times more active than natural human calcitonin.

U.S. Pat. No. 3,849,388 mentions substitution analogs, including position 31 analogs in human calcitonin. The salmon 2 calcitonin analog with Val-, Ala[29] and also Ala[31] and Val[29] have been claimed in U.S. Pat. No. 3,801,561. These analogs are of an equivalent potency as salmon 1 calcitonin. The introduction of Ser[29] and Thr[31] in salmon 2 calcitonin does not increase their activity relative to salmon 1 calcitonin (Maier, R. (1976) Calcif. Tiss. Res. (SUPPL) 317-320).

SUMMARY OF THE INVENTION

I have discovered that calcitonin analogs having amino acid substituents derived from single point mutations of the codons for threonine and valine at position 31 have biological activity of the same type as known calcitonins. Such substituents are Ser, Asp, Asn, Glu, Ile, Pro, Met, Lys, Arg, Leu; Gly or Phe. In mRNA, triplets of three nucleotides, or codons provide the genetic information specifying the amino acid sequence during protein biosynthesis. When one base in a gene is replaced by another (single point mutation) one amino acid is often replaced by another in the amino acid sequence of a peptide. My new peptides differ significantly in structure from known calcitonins in that in our peptides the amino acid sequence does not contain threonine, alanine or valine residue at position 31. These new peptides have good potency and quality when compared with the known calcitonins. The introduction of substituents which are derived from point mutations of the codons of the naturally occurring amino acids result in increased activity of the hormone. This increased activity may be due to favorable conformational structures (e.g., conformational change may increase affinity of amino acid for a receptor).

In the case of threonine found at position 31 in salmon 1 calcitonin, when the first nucleotide of the threonine codon is mutated, the threonine codon may be replaced by the alanine codon so that when the peptide is synthesized alanine will appear at position 31.

Codons for threonine read: ACT, ACC, ACA, ACG

Replacing A with G gives the alanine codons: GCT, GCC, GCA, GCG

Replacing A with C gives proline codons: CCT, CCC, CCA, CCG

Replacing A with T gives serine codons: TCT, TCC, TCA, TCG

Similarly, a point mutation to the second nucleotide of threonine codon may give rise to the following amino acid codons:

Replacing C with T gives isoleucine codons: ATT, ATC, ATA, and a methionine codon: ATG.

Replacing C with A gives asparagine codons: AAT and AAC and lysine codons: AAA and AAG.

Replacing C with G gives the remaining serine codons: AGT and AGC and arginine codons: AGA and AGG. A point mutation in the third nucleotide gives rise to another codon for threonine.

Valine is another amino acid that appears at position 31 in natural calcitonins. Alanine can be derived from valine through a point mutation of the second nucleotide in the valine codons. The codons for valine are GTT, GTC, GTA and GTG. Other point mutations of valine codons give rise to codons for other amino acids. For example:

Replacing G with A gives isoleucine codons: ATT, ATC, ATA and a methionine codon: ATG.

Replacing G with C gives leucine codons: CTT, CTC, CTA and CTG.

Replacing G with T gives phenylalanine codons: TTT and TTC and the remaining leucine codons: TTA, TTG.

Replacing the second nucleotide T with C gives alanine codons: GCT, GCC, GCA and GCG.

Replacing T with A gives aspartic acid codons: GAT and GAC and the glutamic acid codons: GAA, GAG.

Replacing T with G gives glycine codons: GGT, GGC, GGA and GGG. A point mutation in the third nucleotide of the valine codon gives another codon for valine.

It has been observed that the calcitonins with the lowest biological activity have alanine at position 31. This includes human calcitonin. Since the human calcitonins with lower biopotency have alanine at position 31, which could have arisen by a single point mutation in the threonine codon it is tempting to believe that at one time in the evolutionary scheme calcitonin of lower activity was desirable in humans.

The amino acids, Ser, Pro, Ile, Met, Asn, Lys, Arg, Leu, Phe, Asp, Glu and Gly, which also can be generated through a single point mutation from salmon calcitonins or others, do not exist in any known calcitonin. In the homology comparison set forth above, examples are given where these amino acids do occur in several combinations at other positions in the calcitonin sequence. Thus, there are other differences in the amino acid composition of the various calcitonins and it is not yet clear which substitutions relate to activity. However, it is clear that substitutions at position 31 do influence activity.

Although I do not wish to be bound to the following explanation, I think it likely that appropriate amino acid substitutents at position 31 exert an important contribution to increasing the biological activity of the same type as salmon 1 calcitonin, in synthetic calcitonins. This difference in activity can be seen by the selection process which has occurred during the evolutionary process.

Preferred amino acid substituents are Ser, Asp, Asn, Glu. A preferred analog is substituted salmon 1 calcitonin of the formula:

$$H_2N-Cys-Ser-Asn-Leu-Ser-Thr-Cys-Val-Leu-$$
$$\phantom{H_2N-}1\phantom{xx}2\phantom{xxx}3\phantom{xxx}4\phantom{xxx}5\phantom{xxx}6\phantom{xxx}7\phantom{xxx}8\phantom{xxx}9$$

$$-Gly-Lys-Leu-Ser-Gln-Glu-Leu-His-Lys-$$
$$\phantom{-}10\phantom{xx}11\phantom{xxx}12\phantom{xxx}13\phantom{xxx}14\phantom{xxx}15\phantom{xxx}16\phantom{xxx}17\phantom{xxx}18$$

$$-Leu-Gln-Thr-Tyr-Pro-Arg-Thr-Asn-$$
$$\phantom{-}19\phantom{xx}20\phantom{xxx}21\phantom{xxx}22\phantom{xxx}23\phantom{xxx}24\phantom{xxx}25\phantom{xxx}26$$

$$-Thr-Gly-Ser-Gly-X-Pro-NH_2$$
$$\phantom{-}27\phantom{xx}28\phantom{xxx}29\phantom{xxx}30\phantom{xxx}31\phantom{xxx}32$$

in which X is, Ser, Asp, Asn, Glu, Ile, Pro, Met, Lys, Arg, Leu, Gly or Phe. Preferred calcitonin analogs are [Ser$^{31}$] calcitonin, [Asn$^{31}$] calcitonin, [Asp$^{31}$] calcitonin, [Glu$^{31}$] calcitonin. Particularly preferred peptides of the invention are the salmon 1 analogs, especially [Ser$^{31}$] salmon 1 calcitonin, [Asn$^{31}$] salmon 1 calcitonin, [Asp$^{31}$] salmon 1 calcitonin, [Glu$^{31}$] salmon 1 calcitonin.

DESCRIPTION OF THE INVENTION

Resin Peptide Synthesis

The synthesis of calcitonin analogs may follow the stepwise solid phase strategy reported in Merrifield, R. B. (1963) J. Am. Chem. Soc. 85, 2149-2154, the teachings of which are incorporated herein by reference. The acid labile tert-butyloxycarbonyl (Boc-) group may be used for temporary alpha-N protection and the more acid stable groups may be used for protection of the side chains of the amino acids. Amino acid derivatives are listed in Table 1 and abbreviations are listed in Table 2. Attachment of the peptide chain to a copolymer matrix of styrene and 1% divinylbenzene may employ a benzhydrylamine type "handle" as reported in Pietta, P. G. et al. (1970) Chem. Commun. 650-651; Hruby, V. J. et al. (1977) J. Org. Chem. 42, 3552-3556; and Tam, J. P. et al. (1981) Tetrahedron Lett. 22, 2851-2854, which teachings also are incorporated by reference. All amino acids may be incorporated following a double coupling protocol with some modifications for particular amino acids. For all reactions, except for arginine, asparagine and glutamine, the first coupling employs the preformed symmetric anhydride method (Hagenmaier, H. and Frank, H. (1972) Hoppe-Seyler's Z. Physiol. Chem. 353, 1973-1976) in dichloromethane and the second coupling employs the preformed hydroxybenztriazole ester method (König, W. and Geiger, R. (1970) Chem. Ber. 103, 788-798) in dimethyl formamide (DMF). For Boc-Arg(Tos), standard DCC coupling conditions are employed to reduce the risk of lactam formation. The second coupling is done with the active HOBt ester method in DMF. Boc-Asn and Boc-Gln were exclusively coupled as HOBt esters in DMF to reduce nitrile and amidine formation (Mojsov, S. et al. (1980) J. Org. Chem. 45, 555-560). N-epsilon-(2-Chlorobenzyloxycarbonyl)lysine, Lys(ClZ), is used because it is more stable than the benzyloxycarbonyl derivative to the acid deprotection steps and it also avoids side chain branching (Erickson, B. W. and Merrifield, R. B. (1972) J. Am. Chem. Soc. 95, 3757-3763). The beta-cyclohexyl ester (cHex) of Boc-Asp-OH is used; it is also more stable to acids and thus minimizes aspartimide formation (Tam, J. P. (1979) Tetrahedron Lett. 4033-4036). The quantitative ninhydrin reaction is routinely used throughout the synthesis to monitor the extent of coupling after each cycle (Sarin, V. K. et al. (1981) Anal. Biochem. 117, 147-157).

TABLE 1

Amino acid derivatives for synthesis of salmon 1 calcitonin substitution analogs at position 31. [Ser$^{31}$]salmon 1 calcitonin

| cycl nr. and amino acid | protected amino acids | MW | mmol | g | coupling procedure |
|---|---|---|---|---|---|
| 32 | Pro-benzhydryl amine resin | | 1 | 2 | |
| 31,29,13,5,2, | Boc—Ser(Bzl) | 259.1 | 8 | 2.08 | A |
| | | | 4 | 1.04 | |
| 30,28,10 | Boc—Gly | 175.2 | 8 | 1.4 | A |
| | | | 4 | 0.7 | |
| 27,25,21,6 | Boc—Thr(Bzl) | 309.1 | 8 | 2.48 | A |
| | | | 4 | 1.24 | |
| 26,3 | Boc—Asn | 232.2 | 4 | 0.93 | B |
| 24, | Boc—Arg(Tos) | 442.5 | 4 | 1.77 | C |
| 23, | Boc—Pro | 215.1 | 8 | 1.72 | A |
| | | | 4 | 0.86 | |
| 22, | Boc—Tyr(Cl$_2$Bzl) | 441.2 | 8 | 3.53 | A |
| | | | 4 | 1.76 | |
| 20,14 | Boc—Gln | 246.3 | 4 | 0.98 | B |
| 19,16,12,9,4, | Boc—Leu | 249.2 | 8 | 2.0 | A |
| | | | 4 | 1.0 | |
| 18,11 | Boc—Lys(Cl—Z) | 314.8 | 8 | 2.5 | A |
| | | | 4 | 1.26 | |
| 17, | Boc—His(Tos) | 409.2 | 8 | 3.28 | A |
| | | | 4 | 1.64 | |
| 15, | Boc—Glu(OcHex) | 342.4 | 8 | 2.74 | A |
| | | | 4 | 1.37 | |
| 8, | Boc—Val | 217.1 | 8 | 1.74 | A |
| | | | 4 | 0.87 | |
| 7,1, | Boc—Cys(4-Me—Bzl) | 352.2 | 8 | 2.6 | A |
| | | | 4 | 1.3 | |
| [Asn$^{31}$]salmon 1 calcitonin | | | | | |
| 31 | Boc—Asn | 232.2 | 4 | 0.93 | B |

TABLE 2

Abbreviations (Biochem Biophys. Acta 133, 1-5 (1967)).

Boc = tert-butyloxycarbonyl
Bzl = benzyl
Tos = tosyl
Cl$_2$Bzl = 2,6-dichlorobenzyl
Cl—Z = o-chlorobenzyloxycarbonyl
OcHex = gamma-cyclohexyl ester
4-Me—Bzl = 4-methylbenzyl
HOBt = N—hydroxybenztriazole
DIEA = diisopropylethylamine
DCC = dicyclohexylcarbodiimide
DMF = N,N—dimethylformamide
CM = carboxymethyl
TFA = trifluoroacetic acid
HPLC = high performance liquid chromatography
MRC units = Medical Research Council units standard
Pro = L-prolyl
Ser = L-seryl
Gly = L-glycyl
Thr = L-threonyl
Asn = L-asparaginyl
Arg = L-arginyl TABLE 2-continued Abbreviations (Biochem Biophys. Acta 133, 1-5 (1967)).

Tyr = L-thyronyl
Gln = L-glutaminyl
Leu = L-leucyl
Lys = L-lysyl
His = L-histidyl
Glu = L-glutamyl
Val = L-valyl
Cys = L-cysteinyl
A = deoxyadenosine
G = deoxyguanosine
C = deoxycytidine
T = thymidine Resin Peptide Cleavage and Purification Cleavage of the peptides from the resin and removal of all the remaining protecting groups is accomplished by treatment with anhydrous hydrogen fluoride in the presence of anisole (Yamashiro, D. and Li, C. H. (1978) J. Am. Chem. Soc. 100, 5174-5179). Crude peptide is removed from the resin by washing with 10% aqueous acetic acid. After lyophilization, the residue may be treated with dithiothreitol (Cleland, W. W. (1964) Biochemistry 3, 480-482) in sodium phosphate buffer at pH 7.5. The intramolecular disulfide bond in calcitonin between cysteine residues 1 and 7 can be formed by diluting the solution several-fold and adding potassium-ferricyanide in aqueous solution. The resultant peptide solution is then concentrated by passing it through a CM-Sephadex, C-25 column and then eluting with a linear gradient of sodium chloride from zero to 0.3 molar in the same phosphate buffer (Live, D. H. et al. (1977) J. Org. Chem. 42, 3556-3561; Moe, G. R. and Kaiser, E. T. (1985) Biochemistry 24, 1971-1976). The sample is finally desalted by gel filtration, concentrated and isolated by HPLC.

While the substitution analogs at position 31 may be made in salmon, eel, chicken, bovine, porcine, murine, ovine and human calcitonin, for exemplification, the following detailed disclosure is directed to salmon 1 calcitonin. The formula for our new substitution analogs at position 31 of salmon 1 calcitonin having activity of the same type as known calcitonin may be written as follows:

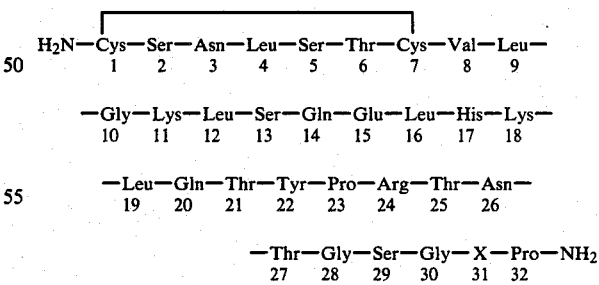

in which
X=Ser, Asp, Asn, Glu, Ile, Pro, Met, Lys, Arg, Leu Phe or Gly.

As may be seen from the formula above, 32 amino acids are involved and in this formula, the positions are numbered according to the accepted procedure beginning at position 1 for the cysteine on one end of the chain and ending with proline amide at position 32 at the other end of the chain. For clarity of description, this same numbering system will be followed in referring to the cycles of the synthesis. The assembly of the amino acids begins with cycle 31 which involves the coupling of the amino acid to the proline moiety, followed by residue 30 and so on to the last amino acid. Protected amino acid derivatives that may be used in the synthesis of calcitonin analogs are given in Table 1. The resin which is functionalized with proline is available from chemical supply houses.

As indicated earlier, three types of coupling procedures are used, depending on the properties of reactants. In Table 1, the amino acid position and cycle number, type of coupling procedure, molecular weights and amount of reactants for the cycle are given. The details for each coupling protocol A, B and C are described below.

RESIN PEPTIDE SYNTHESIS

EXAMPLE 1

[Ser$^{31}$] salmon 1 calcitonin: Double coupling protocol using symmetric anhydride and active ester methods may be used to ensure as complete coupling as possible. The following protocol may be used for all amino acids except for arginine, asparagine and glutamine. The protocol is given for 2 g benzhydryl type resin functionalized with a total of 1 mMol of proline.

Coupling Procedure A.
1. The resin is washed with dichloromethane, $CH_2Cl_2$, (30 mL, 6×1 min).
2. Removal of the Boc protecting group is done with 50% TFA in $CH_2Cl_2$ (30 mL, 3×1 min) and with 30 mL for 20 min.
3. The reagent is then removed with $CH_2Cl_2$ wash (30 mL, 6×1 min).
4. Traces of acid are finally removed with 5% DIEA in $CH_2Cl_2$ (30 mL, 2×2 min).
5. A final wash is done before the coupling is completed, $CH_2Cl_2$ (30 mL, 6×1 min).
6. 5 mg of the resin are removed for ninhydrin test.
7. The protected amino acid (listed in Table 1, 8 mMol) dissolved in 10 mL of $CH_2Cl_2$ is treated with DCC (4 mMol, 825 mg) in 3 mL of $CH_2Cl_2$. After 10 min, the solution is filtered and added to the resin. The precipitate is washed with 10 mL of $CH_2Cl_2$ and added to the reaction vessel which is then shaken for 2 h at room temperature.
8. The resin is washed with $CH_2Cl_2$ (30 mL, 4×2 min).
9. The resin is washed with 5% DIEA in $CH_2Cl_2$ (30 mL, 2 min).
10. The resin is washed with $CH_2Cl_2$ (30 mL, 4×2 min).
11. Ninhydrin test is performed.
12. The resin is washed with DMF (30 mL, 2×2 min).
13. HOBt (4 mMol, 540 mg) in 7 mL of DMF at 0° C. is mixed with DCC (4 mMol, 825 mg) in 3 mL $CH_2Cl_2$. The protected amino acid (listed in Table 1, 4 mMol) dissolved in 6 mL of DMF is then added. The mixture is kept for 10 min at 0° C. and is then added to the resin. The mixture is shaken for 2 h at room temperature.
14. The resin is then washed with DMF (30 mL, 2×2 min).
15. The resin is washed with $CH_2Cl_2$ (30 mL, 4×1 min).
16. The resin is washed with 5% DIEA in $CH_2Cl_2$ (30 mL, 2 min).
17. The resin is washed with $CH_2Cl_2$ (30 mL, 3×1 min).
18. Ninhydrin test is performed.

Coupling Procedure B.
(Used for the amino acids asparagine and glutamine):
Steps 1–6 were the same as coupling procedure A.
7. The resin is washed with DMF in $CH_2Cl_2$ (1:2 v/v, 30 mL, 2×2 min).
8. To HOBt (4 mMol, 540 mg) in 7 mL DMF/$CH_2Cl_2$ (1:1 v/v) at 0° C. is added DCC (4 mMol, 825 mg) in 3 mL of $CH_2Cl_2$. To that mixture is then added the protected amino acid (listed in Table 1, 4 mMol) in 6 mL of DMF/$CH_2Cl_2$. The reaction mixture is added to the resin after 10 min at 0° C. The resin is then shaken for 2 h at room temperature.
9. The resin is washed with DMF/$CH_2Cl_2$ (1:2 v/v, 30 mL, 2×2 min).

The steps 8–18 described in coupling procedure A are than followed.

Coupling Procedure C.
(Used for the amino acid arginine):
Steps 1–6 are the same as coupling procedure A.
7. The protected amino acid (listed in Table 1, 4 mMol) in 10 mL $CH_2Cl_2$ is added to the resin. DCC (4 mMol, 825 mg) in 3 mL $CH_2Cl_2$ is added after 5 min to the resin. The reaction mixture is then shaken for 2 h at room temperature.

The steps 8–18 described in coupling procedure A are then followed.

EXAMPLE 2

[Asn$^{31}$] salmon 1 calcitonin: Boc-Asn is used in cycle 31, and coupling procedure B is employed. The preceding couplings were the same as previously described (Table 1).

In each example, the addition of Cys$^1$ represents the completion of the solid phase synthesis. The Boc group is finally removed by steps 1–6 in coupling procedure A. The resin peptides are then removed from the reaction vessel and dried in vacuum. Cleavage and purification steps are carried out as follows:

RESIN-PEPTIDE CLEAVAGE

The dried resin peptide (2 g) and 2 mL of anisole are placed in a teflon reaction vessel which is cooled in a dry ice-acetone bath and about 15 mL of hydrogen fluoride gas is condensed into the vessel. The mixture is stirred at 0° C. in an ice bath for 45 min. The hydrogen fluoride is then evaporated under vacuum, using first a water aspirator and later a high vacuum pump. The residue is triturated with 5×30 mL of ethyl acetate, and the peptide was extracted from the resin beads with 100 mL of 10% aqueous acetic acid solution. The mixture was lyophilized to dryness.

PURIFICATION OF CRUDE PEPTIDES

A 100 mg sample of the lyophilized peptide is treated with excess dithiothreitol (5 mMol) in 5 mL of 50 mM sodium phosphate buffer at pH 7.5 for 1 h at room temperature. The intramolecular disulfide bond between cysteine residues 1 and 7 is formed by diluting the peptide solution to a volume of 1 liter in the same buffer. A solution of 20 mM $K_3Fe(CN)_6$ is slowly added with stirring until a persistant yellow color is obtained. The resultant dilute peptide solution is concentrated by passing it through a CM-Sephadex, C-25 column and then eluting with a linear gradient of NaCl from zero to 0.3M employing the same buffer. Fractions from this column may be desalted on a Sephadex G-15 column, eluting with a 0.03M aqueous acetic acid solution. Samples for biological testing are isolated on an analytical HPLC (column: Altex ODS, 5 micron, 4.6×250 mm, flow 1.5 mL/min, gradient of 30–45% acetonitrile in 0.1M ammonium acetate buffer at pH 5.5). The isolated samples may be quantified using salmon 1 calcitonin as reference sample.

The HPLC isolated samples are hydrolyzed with 5.5M hydrochloric acid, and amino acid analyses are performed to confirm the chemical composition.

The new polypeptides are biologically active and are useful in lowering the content of calcium in the plasma, as indicated by standard tests in rats (Kumar, M. A. et al. (1965) J. Endocrinology 33, 469–475). While only certain embodiments of our invention have been described in specific details, it will be apparent to those skilled in the art that many other specific embodiments may be practiced and many changes may be made, all within the spirit of the invention and the scope of the appended claims.

What is claimed is:

1. A biologically active calcitonin having 32 amino acid residues with a C-terminal prolinamide and a N-terminal disulfide linked ring from position 1 through 7 and having at position 31 an amino acid substitutent which is Ser, Asp, Asn, Glu, Ile, Pro, Met, Lys, Arg, Leu, Phe or Gly.

2. The compound of claim 1 wherein the calcitonin is [Ser$^{31}$] salmon 1 calcitonin.

3. The compound of claim 1 wherein the calcitonin is [Asp$^{31}$] salmon 1 calcitonin.

4. The compound of claim 1 wherein the calcitonin is [Asn$^{31}$] salmon 1 calcitonin.

5. The compounds of claim 1 wherein the calcitonin is [Glu$^{31}$] salmon 1 calcitonin.

6. The compound of claim 1 wherein the calcitonin is salmon, eel, chicken, bovine, porcine, ovine, murine or human calcitonin.

7. [Ser$^{31}$] calcitonin.

8. [Asp$^{31}$] calcitonin.

9. [Asn$^{31}$] calcitonin.

10. [Glu$^{31}$] calcitonin.

11. The compound of claim 1 wherein the calcitonin has the ability to lower the content of calcium in plasma.

* * * * *